United States Patent [19]

Belzer et al.

[11] Patent Number: 4,879,283

[45] Date of Patent: * Nov. 7, 1989

[54] SOLUTION FOR THE PRESERVATION OF ORGANS

[75] Inventors: Folkert D. Belzer; James H. Southard, both of Madison, Wis.

[73] Assignee: Wisconsin Alumni Research Foundation, Madison, Wis.

[*] Notice: The portion of the term of this patent subsequent to Jan. 17, 2006 has been disclaimed.

[21] Appl. No.: 139,530

[22] Filed: Dec. 29, 1987

Related U.S. Application Data

[63] Continuation-in-part of Ser. No. 784,435, Oct. 3, 1985, Pat. No. 4,798,824.

[51] Int. Cl.$^4$ ............................................. A61K 31/715
[52] U.S. Cl. ..................................... 514/60; 514/832; 435/1; 435/283
[58] Field of Search .......................... 514/3, 4, 60, 832; 435/1, 283

[56] References Cited

U.S. PATENT DOCUMENTS 3,523,938  8/1970  Hershenson et al. ................ 536/111

FOREIGN PATENT DOCUMENTS 3030863  3/1982  Fed. Rep. of Germany ........ 514/60

*Primary Examiner*—John W. Rollins
*Attorney, Agent, or Firm*—Howard W. Bremer

[57] ABSTRACT

In accordance with the present invention a method of preserving organs using a perfusate or storage solution containing a specific synthetic hydroxyethyl starch in place of human serum albumin is disclosed. A suitable composition is provided. Disclosed is a cold-storage solution and perfusate that has provided 72 hour preservation for the pancreas, 48 hour storage for the kidney and at least 24 hour preservation for the liver.

12 Claims, No Drawings

SOLUTION FOR THE PRESERVATION OF ORGANS

This application is a continuation-in-part of U.S. Ser. No. 784,435, filed Oct. 3, 1985 now U.S. Pat. No. 4,798,824.

BACKGROUND OF THE INVENTION

Renal preservation, the ex vivo storage of cadaveric kidneys, is a relatively new field. Preservation of cadaveric kidneys for transplantation is common practice in hospitals; however, advances have been limited to trial and error experimentation. Although this approach has been partially successful from a clinical standpoint, the actual principles behind these successes are not well understood.

As renal transplantation has evolved from a strictly research procedure to an established clinical therapy for end-stage renal disease, renal preservation has progressed from the laboratory research stage to an established clinical method. At present, the two most commonly used methods for renal preservation are simple hypothermic storage and continuous perfusion. With simple hypothermic storage, the most common method of clinical renal preservation, the organs are removed from the cadaver donor and are cooled rapidly. This is usually achieved by a combination of external cooling and a short period of perfusion to drop the core temperature as quickly as possible. The kidneys are then stored, immersed in a flush-out solution in a simple plastic container, and kept at a temperature of 0° to 4° C. by immersing the container in ice. The advantages of this method are its simplicity, its low cost, and the ease of transportation of the organs. The composition of the flush-out solution to provide optimum preservation has been extensively studied.

The second method of renal preservation which has undergone extensive laboratory investigation, as well as clinical testing, is continuous pulsatile perfusion. The basic ingredients of the continuous perfusion are (1) pulsatile flow, (2) hypothermia, (3) membrane oxygenation, and (4) a perfusate containing both albumin and lipids. With minor modifications, all presently used clinical preservation units share these basic principles. There are several advantages to continuous perfusion in clinical transplantation. First, perfusion provides enough time to make cadaveric transplantation a partly elective procedure. Second, it allows viability testing prior to implantation. A significant improvement in the results of cadaveric renal transplantation could be expected if the preservation time could be extended to the five to seven days required for present methods of mixed lymphocyte culture testing.

The ability to successfully preserve human kidneys for two to three days to either simple cold storage after initial flushing with an intracellular electrolyte solution or by pulsatile perfusion with an electrolyte-protein solution has allowed sufficient time for histo-compatibility testing of the donor and recipient, kidney sharing among transplant centers, careful preoperative preparation of the recipient, time for preliminary donor culture results to become available, and vascular repairs of the kidney grant prior to implantation. Kidneys preserved for 72 hours using hypothermic pulsatile perfusion with cryoprecipitated plasma proved to be a significant advance for human kidney preservation and was the preferred method of preservation. Kidney organ preservation with ice-cold intracellular electrolyte flush solution followed by simple cold storage has been satisfactorily employed for human kidney preservation for up to 61 hours.

Serum albumin, in various forms, is used exclusively for clinical organ preservation to produce the necessary oncotic pressure. These forms include cryoprecipitated plasma, plasma protein fraction, human serum albumin, and silica gel-treated plasma. However, because these perfusates are prepared from naturally derived materials, variation is unavoidable. It would be particularly advantageous if a perfusate containing a synthetic colloid was available.

In the past, a large number of synthetic colloidal materials have been experimentally tested for effectiveness in kidney preservation. These colloids include dextrans, polyvinyl pyrrolidine, pluronics, hydroxyethyl starch (HES), Ficoll, gum arabic, and polyethylene glycol. None of these were as effective as serum albumin. However, HES was effective for 24 hours of preservation and in some cases for 72 hours of preservation. These colloidal materials were all tested in saline-based perfusates. Recently, excellent 72-hour preservation of canine kidney was observed with a perfusate containing gluconate anions in place of chloride with human serum albumin (HSA) for colloid osmotic support.

In the late 1960's two important studies demonstrated that kidneys could be safely preserved for 30 hours by cold storage (1) and for as long as 72 hours by continuous perfusion (2). These two studies changed the clinical transplantation of cadaveric kidneys from an emergency procedure to a semi-elective procedure. Many investigators have tested other cold-storage solutions (3), and some have claimed successful preservation for 48 or 72 hours (3-5). However, Collins solution, or the modified Eurocollins solution (5), is preferred by most transplant centers that preserve kidneys by cold-storage.

The introduction of cyclosporine for immunosupressing during the 1980s revived interest in transplanting other organs, specifically, the liver, pancreas, heart, lung, and heart-lung. But preservation methods that are successful for kidneys have proved unsuccessful for these other organs. Consequently, the clinical preservation of the heart, liver, and pancreas are kept to a minimum and to no longer than 6 to 10 hours. These organs are orders of magnitude more complex to transplant than kidneys, and invariably the operations are performed during the night when operating rooms are available in the donor hospitals. Short preservation times for heart and liver also necessitate two surgical teams, one for the donor and another for the recipient. Extending preservation time for these organs to 30 hours would have the same impact on their transplantation as it did on kidney transplantation, namely, increasing organ availability, decreasing organ wastage, increasing organ sharing, and reducing cost.

A preservation solution useful for all donor organs, both for in situ organ cooling in the donor and for cold storage after the organ is harvested would be desirable.

SUMMARY OF THE INVENTION

In accordance with the present invention a method of preserving organs using a perfusate or storage solution containing a specific synthetic HES in place of human serum albumin is disclosed. A suitable composition is provided. Disclosed is a cold-storage solution and perfusate that has provided 72 hour preservation for the pancreas, 48 hour storage for the kidney and at least 24 hour preservation for the liver.

As indicated hereinabove, serum albumin (HSA) based perfusates have been the standard for preservation of kidneys both experimentally and clinically for the past 17 years. Unfortunately, preservation periods of only three days could be obtained with these types of perfusates. Although both of these methods preserve kidney viability for up to three days, longer preservation times are difficult to obtain consistently. Moreover, even though these methods preserve viability for up to three days, the kidneys are damaged as indicated by the elevated post-transplantation serum creatinine levels and time required to return those elevated levels to normal. Early perfusates were chosen from electrolyte solutions readily available for intravenous infusion and were basically of extracellular composition.

Heretofore, acceptable methods for renal preservation have not been available. Those that have been proven clinically effective are limited to short-time storage (three days) and significantly reduced viability. The present invention describes the biochemical composition of the perfusate and storage solution best suited for the hypothermically preserved organs and a novel synthetic colloid osmotic agent that yields significantly improved long-term preservation.

DETAILED DESCRIPTION OF THE INVENTION

Freezing and continuous aerobic perfusion are theoretically the only means of obtaining truly long-term preservation (from a month to years). Simple cold storage has a specific time limit beyond which the organ is no longer viable. Hypothermia decreases the rate at which intracellular enzymes degrade essential cellular components necessary for organ viability. Hypothermia does not stop metabolism; rather, it simply slows reaction rates and cell death.

Calme, et al., Brit. Med. J. 1963; 2: 651–655, showed that the simple cooling of ischemic kidneys with cold blood preserved function for 12 hours. Collins (Lancet 1969; 2: 1219–1222) showed that using an appropriate flush-out solution further increased storage time for kidneys by a factor of 3 (to 30 hours). The failure of this solution to preserve other organs, such as the pancreas, liver, and heart, is believed to be due to organ-specific metabolic differences.

To be appropriate and effective, the flush-out solution must have a composition that (1) minimizes hypothermic-induced cell swelling, (2) prevents intracellular acidosis, (3) prevents the expansion of extracellular space during the flush-out period, (4) prevents injury from oxygen-free radicals, especially during reperfusion, and (5) provides substrates for regenerating high-energy phosphate compounds during reperfusion.

Hypothermic-induced cell swelling is due to the accumulation of water. This tendency to swell can be counteracted by adding 110 to 140 mmol (110 to 140 mOsm/kg osmotic force) of substances that are impermeable to the cell (impermeants). This concentration of impermeants approximately equals the concentration of glucose in Collins cold-storage solution (120 mM) and of impermeants in other cold-storage solutions. Thus a key component of successful cold-storage solutions is the appropriate concentration of an effective impermeant.

A second important consideration for successful cold storage is the prevention of intracellular acidosis. Ischemia, even in the cold, stimulates glycolysis and glycogenolysis (Pasteur effect); it also increases the production of lactic acid and the concentration of hydrogen ions. Tissue acidosis is fatal to cells and can induce lysisomal instability, activate lysosomal enzymes, and alter mitochondrial properties. The prevention of intracellular acidosis is, therefore, an important prerequisite for good preservation. Some studies have shown that the effective buffering of cold-storage solutions or the use of flush-out solutions with an alkaline pH improves the storage of livers (Lie, TS et al., Transplant Proc. 1984, 16: 134–137) and pancreases (Abstract, Am. Soc. of Transplant Surgeons 13th Annula Meeting, May 28–29, 1987).

An effective cold flush-out solution must prevent the expansion of the extracellular space, expansion that can occur during the in situ flushing of donor organs and after the organs have been harvested. Such expansion can compress the capillary system and cause the flush-out solution to be poorly distributed in the tissue. Most cold-storage solutions do not contain substances that exert oncotic support (albumin or other colloids). The components of the flush-out solution, therefore, rapidly diffuse into extracellular spaces and cause tissue edema. Thus, the ideal in situ flush-out solution should contain substances that create colloidal osmotic pressure, and allows the free exchange of essential constituents of the flush-out solution without expanding the extracellular space.

A fourth important consideration for effective cold storage is injury from oxygen-free radicals during reperfusion; but the exact role of these agents is still unclear. It is believed that oxygen-free radicals may be of little significance in human livers and kidneys because endogenous xanthine oxidase has a relatively low activity compared with the high endogenous activity of superoxide dismutase, which scavenges superoxide anions. In contrast, injury induced by oxygen-free radicals may be extremely important in lungs and intestines, which are sensitive to such damage.

A final important consideration is energy metabolism. Adenosine triphosphate (ATP) rapidly degrades during hypothermic storage, and this degradation results in the formation of end products (adenosine, inosine, and hypoxanthine) to which the plasma membrane is freely permeable. Organ reperfusion necessitates the rapid regeneration of Na-pump activity, which requires ATP. The availability of ATP precursors, therefore, may be important for successful organ preservation.

There are important differences in the metabolism of the kidney, liver, and pancreas, and these differences may influence how well these organs are preserved. The suppression of cell swelling necessitates the use of an effective impermeant. Glucose, the main impermeant in Collins solution is not effective for the liver or pancreas and readily enters cells, Southard, et al., Cryobiology 1986; 23: 477–482. Mannitol, another commonly used impermeant, is about as permeable as glucose in the liver. Thus, one reason why cold-storage solutions that depend on glucose or mannitol are not effective for the liver and pancreas is that these solutions do not contain effective impermeants.

In accordance with the present invention, the solution for preservation of organs contains the anion lactobionate and raffinose as impermeants to the cell, has a solution osmolality of about 320 mOsm/L, $K^+$ of 120 mM and $Na^+$ of 30 mM. The preferred colloid is a modified hydroxyethyl starch having a weight average molecular weight of from about 150,000 to about 350,000 daltons and degree of substitution of from about 0.4 to about 0.7. A more preferred colloid is hydroxyethyl starch having a weight average molecular weight of from about 200,000 to about 300,000 daltons. The preferred colloid is substantially free of hydroxyethyl starch having a molecular weight of less than about 50,000 daltons. In accordance with one embodiment of the present invention, the hydroxyethyl starch is dialyzed against distilled-deionized water or otherwise treated to remove several contaminants previously unknown to have an adverse affect on the effectiveness of hydroxyethyl starch preparations. The materials removed by the dialysis process are the very smallest hydroxyethyl starch components, including the ethylene glycol and ethylene chlorohydrin side products of the hydroxyethylation as well as the residual acetone and sodium chloride. Ethylene glycol and ethylene chlorohydrin are known to be toxic. Hence, their removal, even if present in small amount, is desirable.

In a preferred embodiment, the preservation solution and perfusate composition includes, but is not limited to, the following:

TABLE 1

| Substance | Amount in 1 Liter |
|---|---|
| $K^+$ — lactobionate | 100 mmol |
| $KH_2PO_4$ | 25 mmol |
| $MgSO_4$ | 5 mmol |
| Raffinose | 30 mmol |
| Adenosine | 5 mmol |
| Glutathione | 3 mmol |
| Insulin | 100 U |
| Bactrim | 0.5 mL |
| Dexamethasone | 8 mg |
| Allopurinol | 1 mM |
| Hydroxyethyl starch having a molecular weight of about 200,000 to about 300,000 daltons and a degree of substitution of from about 0.4 to 0.7 | 50 g |

The solution is brought to pH 7.4 at room temperature with NaOH. The final concentrations are Na=30±5 mM, $K^+$=120±5 mM, mOsm/liter=320±5. Bactrim=trimethoprim (16mg/mL) and sulfamethoxazole (80 mg/mL). The hydroxyethyl starch can be present in the range of about 3 to 8%.

Accordingly, the present invention provides extended clinical organ preservation time and, as a synthetic colloid, minimizes the variation which results from persurfates prepared from naturally derived materials.

The present invention has been described in detail and with particular reference to the preferred embodiments; however, it will be understood by one having ordinary skill in the art that changes can be made thereto without departing from the spirit and scope thereof.

EXAMPLE 1

Preparation of Hydroxyethyl Starch

One hundred grams of hydroxyethyl starch were dissolved in one liter of distilled-deionized water to make a 10% w/w solution. The HES solution was placed in dialysis bags (34 mm×18 inches) having a molecular weight cut-off of 50,000 daltons, placed in a 10–15 liter container of distilled-deionized water, and stirred for 72 hours. The water was changed daily, and the HES was collected and frozen at −20° C. until used.

EXAMPLE 2

72-Hour Preservation of Canine Pancreas

Female mongrel dogs weighing 15–25 kg were used for the experiment.

Operative procedure. Anesthesia was induced with pentathol and maintained with halothane. Through a midline incision, the left segment (tail) of the pancreas was harvested as previously described. The graft with the spleen attached was transplanted to the iliac vessels either immediately after flushout (control) or after 48 and 72 hours of cold storage. The pancreatic duct was left open allowing pancreatic juices to drain freely into the abdominal cavity. No anticoagulants were used. The right segment of the pancreas was removed at the time of transplantation.

Experimental protocol. All dogs received 0.5 g Mandol I.V. before harvest and during the first three days posttransplantation. Dogs were fed a standard dog food diet containing Viokase. The animals were divided into three groups. Group I (control): After harvesting and washout, the grafts were immediately transplanted; group 2 (48-hour cold storage); group 3 1 (72-hour cold storage). Blood glucose concentration was determined daily during the first posttransplant week, and biweekly thereafter. Intravenous glucose tolerance test (IVGTT) was performed 24 hours, 2 weeks, and 4 weeks after transplantation. The grafts were removed after 4 weeks, and 2–3 days later an IVGTT was performed. For the IVGTT, glucose (0.5 g/kg body weight) was injected and blood glucose determined after 1, 5, 10, 20, 30, 60, 90, and 120 minutes. The K value was calculated from the blood glucose concentration obtained from the 5–60 minute measurements (9). Glucose values greater than 150 mg/% for more than 2 days and a K value less than 1.0 were considered signs of diabetes.

Preservation. The composition of the preservation solution is shown in Table 1. After removal, the pancreas was flushed with approximately 250–300 mL of flushout solution from a height of 60 cm. The graft was placed in a double plastic bag, covered with preservation solution, and placed in an ice-water bath.

Statistics. Statistical evaluation was made using the student's T test. The values given are means ±SEM.

RESULTS

All grafts were well perfused immediately following transplantation. In the preserved grafts, varying degrees of intralobular edema developed after 5–10 minutes of reperfusion. The spleen was well perfused in all cases. As shown in Table 2, five dogs died; three in the control group and two in group 3 (72-hour preserved). The causes of death were unrelated to the transplant and all dogs died with functioning grafts.

At the time of pancreatectomy, all grafts (even controls) showed various degrees of fibrosis, as did the spleen. Arterial and venous thrombosis was not evident in any of the grafts.

Posttransplant blood glucose values and results of IVGTT are shown in Table 2 for each animal. The mean values (±SEM) for each group studied are also shown in Table 2. The mean blood glucose value during the first post-transplant week was highest in group 3 (124±6 mg%) and this value was significantly different (P<0.05) when compared with values for group 1 (94±7 mg%) and group 2 (107±7mg%). The mean K value on day 1 was also signficantly lower (P<0.05) in group 3 (185±0.15%) compared with group 1 (2.44±0.14%) and group 2 (2.53±0.22%). In group 3, the K values tested on days 14 (1.7±0.1%) and 28 (1.61±0.19%) remained similar to the K value on day 1 (P=NS). In groups 1 and 2, the K values declined and at 2 weeks postransplant; there were no significant differences between the three groups. By the fourth week, the K value for group 3 was better than for group 2, but somewhat lower when compared with the control group (statistical significance could not be shown because of the small numbers in group 1).

TABLE 2

Pottransplant Pancreas Function Following Preservation

| Dog No. | Preservation | Blood Glucose 1st week (mg %) | K value: % IVGTT (1 day) | K value: % IVGTT (2 weeks) | K value: % IVGTT (4 weeks) | Remarks |
|---|---|---|---|---|---|---|
| Group 1: | | | | | | |
| 1 | Control | 72.7 ± 6.2 | 1.97 | 2.23 | — | Dead day 27, pleural effusion |
| 2 | Control | 113.1 ± 7.7 | 2.46 | 1.73 | 1.33 | |
| 3 | Control | 104.4 ± 16.5 | 2.65 | — | — | Dead day 5, intra-abdominal abscess |
| 4 | Control | 93.9 ± 9.8 | 2.76 | 1.82 | 2.76 | |
| 5 | Control | 78.5 ± 16.1 | 2.38 | 1.44 | — | Dead day 26, intussusception |
| | Mean | 93.5 ± 7.0 | 2.44 ± 0.14 | 1.81 ± 0.16[b] | 2.05 ± 0.71 | |
| Group 2: | | | | | | |
| 6 | 48 hr CS | 95.3 ± 5.6 | 2.76 | 1.41 | — | Sacrificed day 14 |
| 7 | 48 hr CS | 91.1 ± 7.3 | 2.65 | 1.92 | — | Sacrificed day 14 |
| 8 | 48 hr CS | 108.3 ± 9.9 | 2.56 | 2.15 | 1.11 | |
| 9 | 48 hr CS | 130.4 ± 10.0 | 1.78 | 1.82 | 1.41 | |
| | Mean | 106.5 ± 6.6 | 2.53 ± 0.22 | 1.83 ± 0.15[b] | 1.26 ± 0.15 | |
| Group 3: | | | | | | |
| 10 | 72 hr CS | 113.5 ± 11.8 | 1.47 | 1.52 | 2.30 | |
| 11 | 72 hr CS | 108.7 ± 9.8 | 1.73 | — | — | Dead day 15, pleural effusion |
| 12 | 72 hr CS | 132.9 ± 10.6 | 1.15 | 1.30 | 1.38 | |
| 13 | 72 hr CS | 105.0 ± 9.1 | 2.55 | 2.37 | 1.68 | |
| 14 | 72 hr CS | 118.8 ± 5.3 | 2.02 | — | — | Dead day 5, no obvious reason |
| 15 | 72 hr CS | 143.2 ± 4.0 | 2.16 | 1.97 | 2.03 | |
| 16 | 72 hr CS | 150.0 ± 8.1 | 1.92 | 1.86 | 1.15 | |
| 17 | 72 hr CS | 115.9 ± 11.0 | 1.77 | 1.77 | 1.15 | |
| | Mean | 123.5 ± 5.9[a] | 1.85 ± 0.15[a] | 1.71 ± 0.18 | 1.62 ± 0.19 | |

[a](P <0.05) vs. group 1 and 2
[b](P <0.05) vs. IVGTT day 1

All dogs became hyperglycemic (blood glucose greater than 200 mg%) following removal of the pancreas indicating that the transplanted organ was solely responsible for glucose homeostasis. Four animals from group 3 were observed for long-term survival. One dog died 7 weeks posttransplant from pneumonia, but remained normoglycemic. Two animals were sacrificed at 3 and 4 months, and one dog was kept for 6 months. All showed no signs of diabetes and were normoglycemic.

EXAMPLE 3

24 Hour Liver Preservation

Clinical liver preservation is limited to about 6–10 hours and increasing this to 24 hours or more could have significant impact on liver transplantation. The isolated perfused rabbit liver was used to assess the quality of preservation following cold storage in Collins solution, Cambridge plasma protein fraction (PPF), Marshalls solution, and the solution of the present invention (preservation solution). Bile production during normothermic perfusion of cold stored livers was the most useful parameter of viability and the rate of bile production (mL/100 gm/hr ±SD) in control vs 24 hour cold stored rabbits livers is shown in the table.

| Control | Cambridge PPF | Eurocollins | Marshalls | Preservation Solution |
|---|---|---|---|---|
| 5.4 ± 1.7 | 1.8 ± 0.9 | 1.9 ± 1.3 | 3.1 ± 0.5 | 4.4 ± 0.5 |

The described preservation solution was superior to other cold storage solutions on the basis of bile production after 24 hours cold storage (2°–4° C.) and normothermic reperfusion.

The ultimate test of successful liver preservation is the transplantation model. The preservation solution was, therefore, tested in the canine orthotopic live transplant model. Following simple flush perfusion with the solution, three consecutive canine livers were stored for 24 to 26 hours. Transplantation was performed using a command "cuff" and suture technique. All livers immediately took on a satisfactory appearance and all three dogs woke promptly and were on their feet within 4 hours of the end of the procedure. Platelet counts were normal 6 hours postoperatively. Bilirubin and enzyme values at 6 hours and the subsequent 7 days are recorded in the table (mean ±SD) and show a rapid return of normal liver function. One dog died on postoperative day 5 due to intussusception.

| | 6 Hrs | Day 1 | Day 3 | Day 5 | Day 7 |
|---|---|---|---|---|---|
| Bilirubin mg % | 0.6 ± 0.3 | 0.7 ± 0.6 | 0.9 ± 0.7 | 0.5 ± 0.4 | 0.4 ± 0.2 |
| SGOT | 2148 ± 983 | 1835 ± 1145 | 61 ± 16 | 55 ± 40 | 45 ± 21 |

|  | 6 Hrs | Day 1 | Day 3 | Day 5 | Day 7 |
|---|---|---|---|---|---|
| Alk. Phos. | 186 ± 14 | 217 ± 47 | 273 ± 126 | 311 ± 64 | 315 ± 48 |

EXAMPLE 4

Kidney Preservation

Based on this experience we have investigated the potential usefulness of the described cold storage (CS) solution for kidney preservation and its effect on renal function after reperfusion was investigated: (1) In the isolated perfused dog kidney model (IPK); and (2) in the canine autotransplant model.

(1) Dog kidneys were either cold stored for 48 hours in Eurocollins (EC) or the described cold storage solution (CS). Kidney function was determined during reperfusion with the IPK model using an oxygenated modified albumin containing Krebs-Henseleit solution at 37° C. over a period of 90 minutes. Urine samples were collected every 10 minutes and analyzed. GFR (creatinine clearance), urine/plasma protein (U/P) and fractional sodium reabsorption (% Na) were calculated. Results are shown in Table 3 as means with standard deviations in parenthesis.

Both cold stored kidney groups had decreased renal function at time of reperfusion (compared to control kidneys). In contrast to EC-stored kidneys, CS-stored kidneys improved GFR and sodium reabsorption significantly during IPK. This improvement in function suggests that kidneys preserved in CS are able to repair cold ischemic damage more rapidly than kidneys stored in EC.

(2) Eight consecutive dog kidneys preserved for 48 hours in CS have been autotransplanted. Three animals were sacrificed due to technical complications (arterial thrombosis, intussusception. Posttransplant serum creatinines (means ±SD) of the five survivors are shown in Table 4.

The study indicates good preservation of renal function for 48 hours of cold storage with the CS solution. This solution, therefore, is capable of preserving the kidney, pancreas and liver and can be used for either simple cold storage or continuous perfusion.

What is claimed is:

1. A solution for the preservation and storage of organs intended for implantation in a patient requiring such implantation, comprising:
    a pharmacologically acceptable storage solution having a solution osmolality of about 320 mOsm/liter and including a lactobionate salt; and
    about 5 weight percent hydroxyethyl starch, wherein said starch is substantially free of ethylene glycol, ethylene chlorohydrin, sodium chloride and acetone and has a molecular weight of from about 150,000 to about 350,000 daltons.

2. A solution for the preservation and storage of organs intended for implantation in a patent requiring such implantation, comprising:
    a pharmacologically acceptable storage solution having a solution osmolality of about 320 mOsm/liter; and
    about 3 to 8 weight percent hydroxyethyl starch, wherein said starch is substantially free of ethylene glycol, ethylene chlorohydrin, sodium chloride and acetone and has a molecular weight of from about 150,000 to about 350,000 daltons, and a lactobionate salt.

3. A solution for the preservation and storage of organs intended for implantation in a patient requiring such implantation, comprising:
    a pharmacologically acceptable storage solution having a solution osmolality of about 320 mOsm/liter; and
    about 5 weight percent hydroxyethyl starch, wherein said starch is substantially free of ethylene glycol, ethylene chlorohydrin, sodium chloride and acetone and has a molecular weight of from about 150,000 to about 350,000 daltons and wherein the starch is substantially free of hydroxyethyl starch having a molecular weight of less than about 50,000 daltons.

4. The solution of claim 3 which includes an electrolyte for maintenance of cell viability.

TABLE 3

| Minutes IPK |  | 10 | 30 | 60 | 90 |
|---|---|---|---|---|---|
|  | C* | 12.93 (5.74) | 15.15 (3.00) | 16.00 (4.44) | 12.06 (4.49) |
| Urine Flow | EC | 5.84 (1.81) | 17.48 (8.77) | 24.41 (11.45) | 30.31 (19.86) |
| uL/min. g | CS | 2.52 (1.67) | 6.20 (2.45) | 6.60 (4.79) | 10.53 (4.23) |
|  | C* | 224.96 (88.90) | 240.38 (30.70) | 210.66 (57.77) | 125.48 (31.62) |
| GFR | EC | 8.09 (3.07) | 29.60 (13.60) | 38.32 (18.53) | 37.30 (21.68) |
| ul/min. g | CS | 6.98 (5.46) | 27.23 (13.75) | 28.06 (23.71) | 51.53 (27.20) |
|  | C* | 0.09 (0.02) | 0.10 (0.02) | 0.12 (0.06) | 0.09 (0.02) |
| U/P Ratio | EC | 0.53 (0.19) | 0.43 (0.09) | 0.35 (0.07) | 0.31 (0.15) |
|  | CS | 0.43 (0.02) | 0.58 (0.16) | 0.64 (0.22) | 0.59 (0.23) |
|  | C* | 98.91 (0.81) | 99.15 (0.47) | 99.05 (0.44) | 98.81 (0.48) |
| % Na | EC | 44.34 (4.93) | 55.35 (8.98) | 56.52 (0.11) | 40.54 (20.52) |
|  | CS | 64.09 (21.78) | 85.71 (5.76) | 86.20 (6.76) | 87.87 (12.28) |

*Control kidneys on IPK

TABLE 4

| Days | 0 | 1 | 2 | 3 | 4 | 5 | 6 | 7 | 8 | 9 | 10 |
|---|---|---|---|---|---|---|---|---|---|---|---|
| Serum Creatine (mg %) | 1.3 ±0.2 | 3.1 ±0.7 | 2.5 ±1.1 | 2.4 ±1.0 | 2.2 ±0.9 | 2.0 ±0.8 | 1.6 ±0.5 | 1.6 ±0.4 | 1.4 ±0.3 | 1.4 ±0.3 | 1.2 ±0.3 |

5. The solution of claim 3 which includes a lactobionate salt.

6. The solution of claim 4 including raffinose.

7. A method for the preservation and storage of organs intended for implantation in a patient requiring such implantation, said method comprising:

flushing said organ with a solution having an osmolality of about 320 mOsm/liter and including a lactobionate salt and about 5 weight percent hydroxyethyl starch, said starch being substantially free of ethylene glycol, ethylene chlorohydrin, sodium chloride and acetone and having a molecular weight of from about 150,000 to about 350,000 daltons; and storing said organ in said solution until implantation in said patient.

8. A method for the preservation and storage of organs intended for implantation in a patient requiring such implantation, said method comprising:

flushing said organ with a solution having an osmolality of about 320 mOsm/liter and about 5 weight percent hydroxyethyl starch, said starch being substantially free of ethylene glycol, ethylene chlorohydrin, sodium chloride and acetone and having a molecular weight of from about 150,000 to about 350,000 daltons and being substantially free of hydroxyethyl starch having a molecular weight less than about 50,000 daltons; and storing said organ in said solution until implantation in said patient.

9. The method of claim 8 in which the solution includes an electrolyte for maintenance of cell viability.

10. The method of claim 8 in which the solution includes a lactobionate salt.

11. The method of claim 9 in which the solution includes raffinose.

12. The method of claim 10 in which the solution includes glutathione.

* * * * *

UNITED STATES PATENT AND TRADEMARK OFFICE
CERTIFICATE OF CORRECTION

PATENT NO.   : 4,879,283
DATED        : November 7, 1989
INVENTOR(S)  : Folkert O. Belzer and James H. Southard It is certified that error appears in the above-indentified patent and that said Letters Patent is hereby corrected as shown below:

Column 1, line 4, insert the following:

"This invention was made with United States Government support awarded by the National Institutes of Health (NIH), Grant Numbers: AM 18624, DK 18624, AM 33554, and DK 35143. The United States Government has certain rights in this invention".

Signed and Sealed this

Twenty-sixth Day of October, 1993

Attest:

BRUCE LEHMAN

*Attesting Officer*   Commissioner of Patents and Trademarks